(12) United States Patent
Brotz

(10) Patent No.: US 6,231,228 B1
(45) Date of Patent: May 15, 2001

(54) MELTING POINT DETERMINATION APPARATUS AND METHOD

(76) Inventor: Gregory R. Brotz, P.O. Box 1322, Sheboygan, WI (US) 53081

( * ) Notice: Subject to any disclaimer, the term of this patent is extended or adjusted under 35 U.S.C. 154(b) by 0 days.

(21) Appl. No.: 09/288,156

(22) Filed: Apr. 8, 1999

(51) Int. Cl.[7] .................................................. G01N 25/04
(52) U.S. Cl. ........................ 374/17; 374/22; 250/341.1; 250/341.6
(58) Field of Search ........................... 374/16, 17, 22, 374/19; 250/341.6, 341.1

(56) References Cited

U.S. PATENT DOCUMENTS

| | | | |
|---|---|---|---|
| 3,187,556 | * | 6/1965 | Ehlers ........................ 374/22 |
| 3,203,228 | * | 8/1965 | Macklem ..................... 374/22 |
| 3,889,118 | * | 6/1975 | Walker ........................ 250/341.1 |
| 4,017,194 | * | 4/1977 | Conroy et al. ............... 250/341.1 |
| 4,188,533 | * | 2/1980 | Ashenfelter et al. ......... 250/341.1 |
| 5,092,679 | * | 3/1992 | Brotz ........................... 374/17 |
| 5,288,148 | * | 2/1994 | Rahimzadeh ................ 374/19 |
| 5,750,997 | * | 5/1998 | Matsuda ...................... 250/341.1 |
| 6,037,591 | * | 3/2000 | Neri et al. ................... 250/341.1 |

FOREIGN PATENT DOCUMENTS

| | | | |
|---|---|---|---|
| 2-0208547 | * | 8/1990 | (JP) ............................ 374/16 |
| 4-0143645 | * | 5/1992 | (JP) ............................ 374/16 |

* cited by examiner

Primary Examiner—Diego Gutierrez
Assistant Examiner—Stanley J. Pruchnic, Jr.
(74) Attorney, Agent, or Firm—William Nitkin

(57) ABSTRACT

A device and method is disclosed for determining the melting point of a sample material utilizing an infrared thermometer to measure the indicated temperature of the sample material while under pressure as such sample material is being heated. Upon melting, the sample material is substantially displaced from the field of view of the infrared thermometer by the force of the applied pressure, resulting in a spike in the sensed temperature.

18 Claims, 5 Drawing Sheets

MELTING POINT DETERMINATION APPARATUS AND METHOD

BACKGROUND OF THE INVENTION

1. Field of the Invention

This invention resides in the area of apparatuses and methods used for the determination of melting points of materials and more particularly relates to an apparatus and method which determines the melting point of a sample material by measuring temperature changes of the material until the thickness of the sample material goes to zero under pressure.

2. Description of the Prior Art

Many methods are used to determine melting points of materials. The simplest are types where observers note temperatures at which materials, upon heating, become transparent such methods first involve immersing the particle of material whose melting point is to be determined in a non-solvent which is heated at a known rate. As the heat from the medium is transferred into the particle, at the point where the temperature of the medium is equal to the melting point of the particle, the particle changes its optical transmissibility and also may change its physical shape. The automated recording of temperature while an observer monitors the reflectivity of infrared light directed at material is disclosed in International Application No. PCT/GB90/00751. A problem with many of these prior art melting point determination apparatuses is that they lack accuracy in that they require the judgment of an observer as to when a reaction has taken place, and this judgment can vary from observer to observer.

U.S. Pat. No. 5,092,679 by the present inventor disclosed an apparatus and method that automatically records measurements of both light reflectivity or transmissivity and temperature of a material to determine its melting point. The invention also disclosed means for recording deformation of materials at various pressures.

A November, 1991 article in *Laboratory Equipment Digest* entitled "Faster and Simpler Melting Point Measurement" described a melting point device which measures the reflectivity of near-infrared light directed at a material, which material rests on a plate of borosilicate glass heated from below by a flat film strip heater. A problem with many of the prior art apparatuses is that they require a light source and measure the reflectivity of light directed at the sample material.

SUMMARY OF THE INVENTION

It is an object of the device and method of this invention to determine the melting point of a sample material utilizing a narrow field of view non-contact infrared thermometer hereinafter referred to as an infrared thermometer. The use of such an infrared thermometer allows for a standard temperature scale to be utilized.

It is a further object of this invention to provide a device to determine melting point as it relates to pressure. It is important that pressure be considered when determining a melting point of a material because at different pressures, a material at its melting point may have a variety of states.

The device of this invention utilizes a powder made from the material that is to have its melting point determined. The powdered material is placed between an upper first glass plate and a lower second glass plate to form a wafer which wafer/plate sandwich is supported by a support member disposed under each end of the lower plate on its bottom side. Pressure is first applied to the upper plate. In one embodiment heat is then applied to the upper plate from above and the temperature of the sandwiched wafer is measured by an infrared thermometer positioned under the lower plate. The temperature of the bottom surface of the lower plate is continuously recorded. When the sample material melts, it thins and spreads out, changing the heat transmission properties of the wafer, and is no longer sensed by the infrared thermometer. At that point in time when the infrared thermometer directly senses the heat source, the indicated temperature spikes, and a chart recorder indicates the temperature at that point in time of such temperature spike which corresponds to the melting point of the sample material. Toroidal heat sources can also be utilized in some embodiments above, and in some embodiments below, the plates. Once the sample melts, the toroidal heat source, not being in the direct line of sight of the infrared thermometer which has a narrow field of view, is then not sensed and the indicated temperature detected drops at the melting point of the material which temperature drop is recorded.

DESCRIPTION OF THE PREFERRED EMBODIMENT(S)

Figure 1:
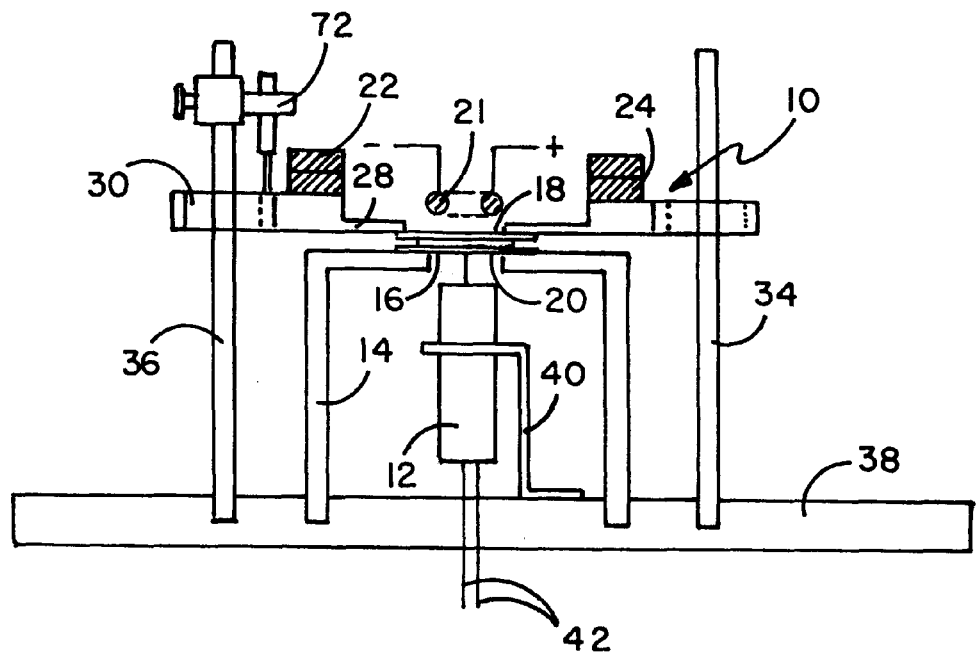
FIG. 1 illustrates a cross-sectional front view of one embodiment of the device of this invention.

FIG. 1 illustrates one embodiment of the device of this invention. A powder of sample material 20 whose melting point is to be determined is dusted on the upper surface of lower plate 16. Lower plate 16 is made of an infrared-transparent and transmissive glass. Such glass can be made from germanium, zinc selenide, or chalcogenide, i.e. sulfur-based glasses. Upper plate 18, which can be made from the same type of glass as lower plate 16, is placed directly over sample material 20 on lower plate 16 to form a wafer. This wafer is supported on support member 14. The bottom of support member 14 is mounted on platform 38. An opening is defined at the top of support member 14 so that sample material 20 is visibly exposed from above and below the upper and lower plates. Infrared thermometer 12 is positioned just below lower plate 16 in order to measure the temperature on the surface of lower plate 16. Infrared thermometer 12 is fixedly mounted to platform 38 by support 40. Heating element 21 is positioned just above upper plate 18 to heat sample material 20. Heating element 21 can be a circular Nichrome heating coil within a reflector which reflector is not shown. Attached to collar 30 is arm 28 which secures the wafer on support member 14 and also applies the desired pressure to sample material 20 through selection of an appropriate weight member 22 which is placed on collar 30. Collar 30 moves vertically along first and second posts 36 and 34, respectively, preventing undesirable lateral movement and assuring the stability of arm 28. The collar, arm and weight members which can only be moved in a vertical direction on first and second posts 36 and 34, respectively, constitute weight support assembly 10, and finction as a means for varying the pressure applied to the sample material depending on the amount of weight utilized. Roller bearing 31, as seen in FIG. 3, can be provided in weight support assembly 10 for it to move easily on first and second posts 36 and 34.

Figure 2:
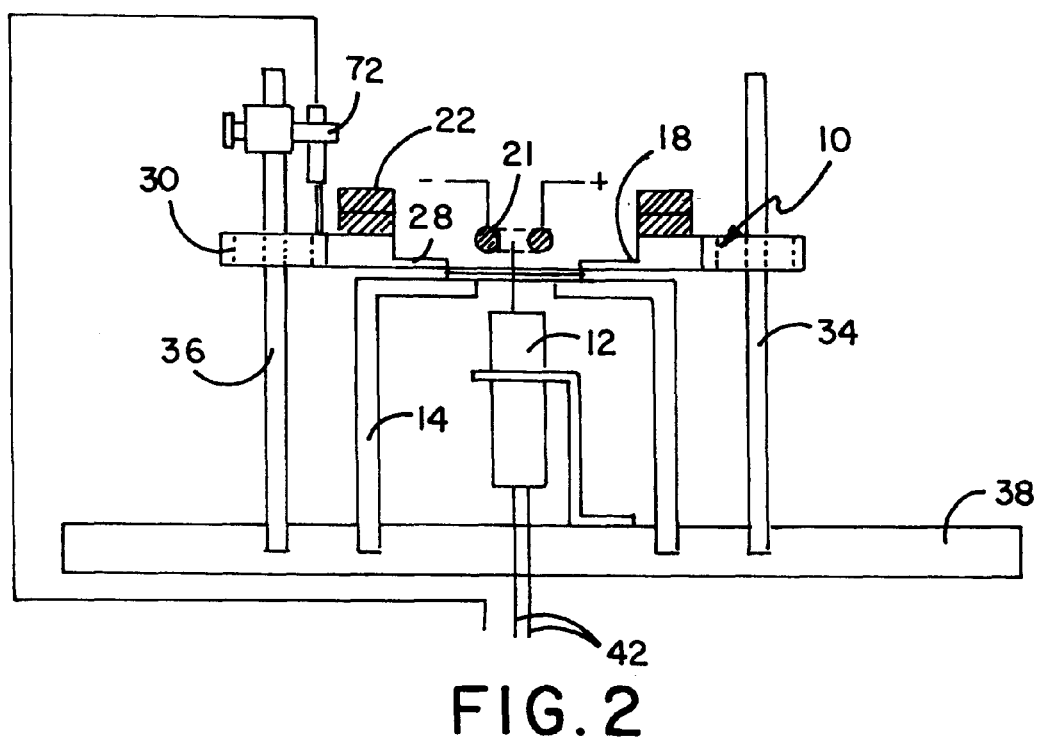
FIG. 2 illustrates the device of FIG. 1 with the sample material melted.
Figure 9:
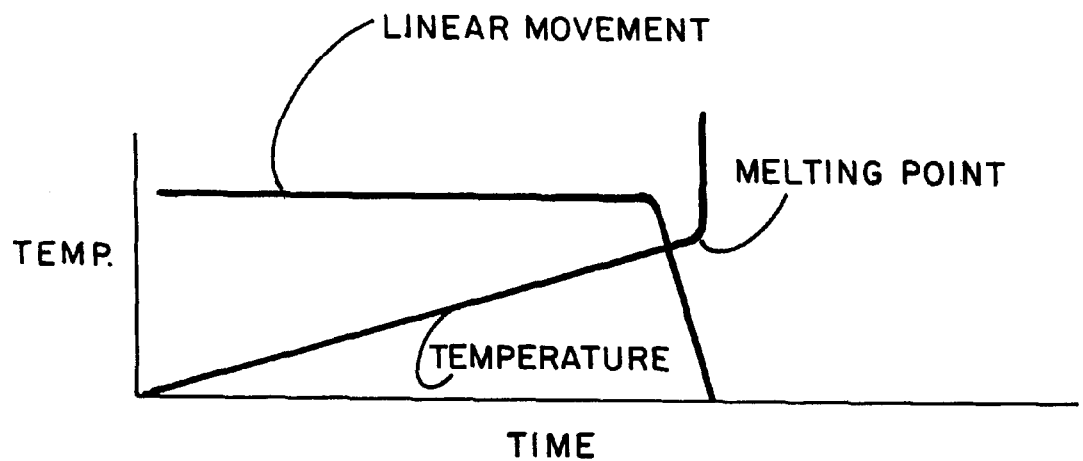
FIG. 9 illustrates a chart showing a typical curve of the recording of a melting point utilizing the device of FIGS. 1 and 2 showing the linear motion sensor output and temperature output.
Figure 10:
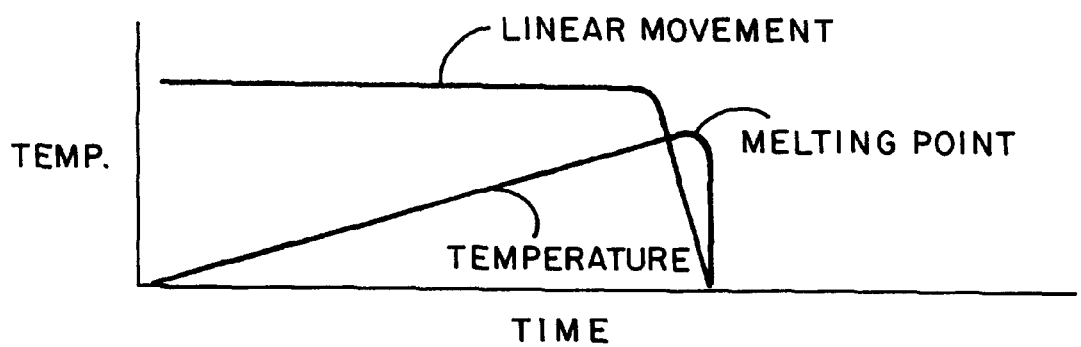
FIG. 10 illustrates a chart showing a typical curve of the recording of a melting point utilizing the device of FIGS. 4 and 6 showing the linear motion sensor output and temperature output.

In practice, the powder of sample material 20 is placed on lower plate 16 and any excess is shaken off. In some cases a silicon oil can be rubbed on the plate's surface to provide some release of the melted powder to the plate. Upper plate 18 is then placed over the sample and lower plate 16 to form a wafer. The wafer is positioned on support member 14. Weight support assembly 10 is lowered so that arm 28, which can be horizontally disposed as shown or disposed at a downward angle as in FIGS. 3–6, rests on the edges of upper plate 18. A desired amount of weight, such as in the form of first and second weight members 22 and 24, is added onto weight support assembly 10. Infrared thermometer 12 is then turned on and begins relaying temperature readings to a strip chart recorder through wires 42. Heating element 21, which can have a reflector (not shown) above it, directs infrared radiation through infrared transmissive upper plate 18 to sample material 20. The sample material is in most cases infrared absorbing or at least more absorbing than the wafer plates and so rises in temperature. Lower plate 16 is likewise infrared transmissive and because of this the non-contact thermometer is actually viewing the lower surface of the sample material and so measuring the temperature of the sample material directly. Sample material 20 is heated to its melting point, when the particles that make up the powder fuse and clarify. At the melting point, as seen in FIG. 2, sample material 20 in the molten state is forced out the ends of upper and lower plates 18 and 16 by the pressure from first and second weight members 22 and 24. When the melting point of sample material 20 is reached, non-contact infrared thermometer 12 aimed toward lower plate 16 will no longer sense the temperature of the sample material but of the much hotter heating element 21, and there will be an abrupt change in the temperature readout. Thus at the material's melting point when heating element 21 is exposed to infrared thermometer 12, as seen in FIG. 2, there will be a sharp increase in indicated temperature. This sharp increase in indicated temperature is represented by a spike on the plot of temperature versus time in the chart of FIG. 7 which represents the melting point of the sample material. Linear motion sensor 72 detects the movement of weight support assembly 10 which movement can be plotted on the same chart recorder as the temperature readout as depicted in the chart of FIG. 9. All of the devices herein can be equipped with a lateral rotating carousel having multiple wells containing wafers of the same sample material or of different sample material. There are advantages in making determinations of several wafers of the same sample material and then averaging the results.

Figure 3:
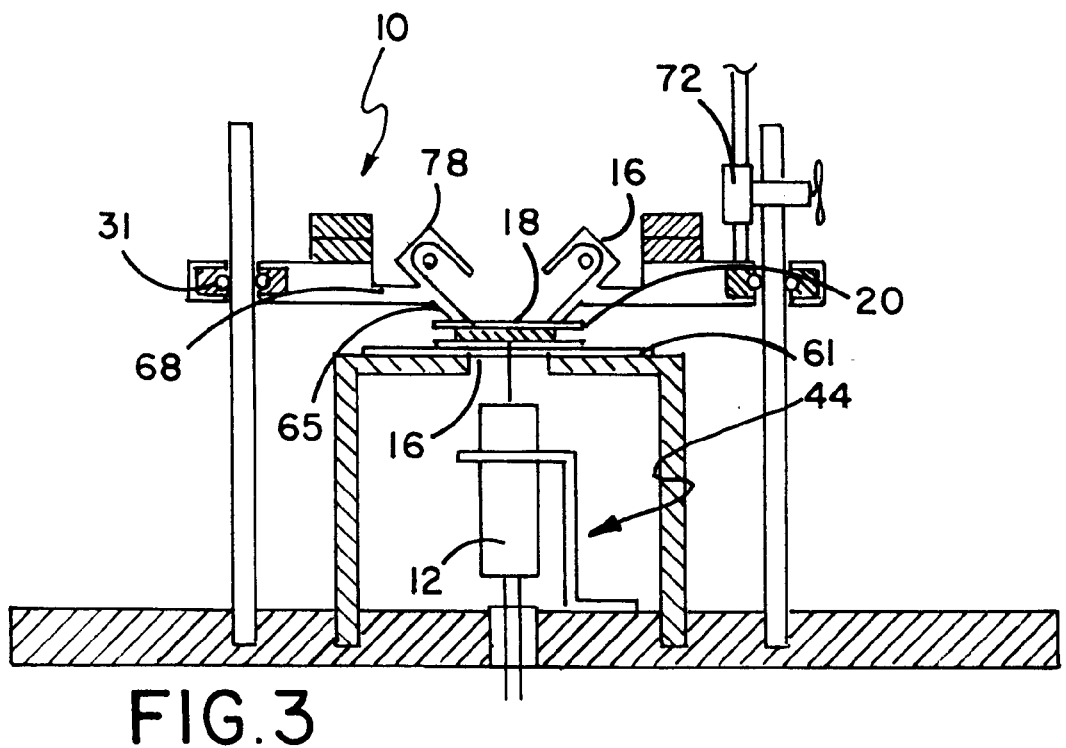
FIG. 3 illustrates a cross-sectional side view of a further alternate embodiment of the device of this invention.
Figure 4:
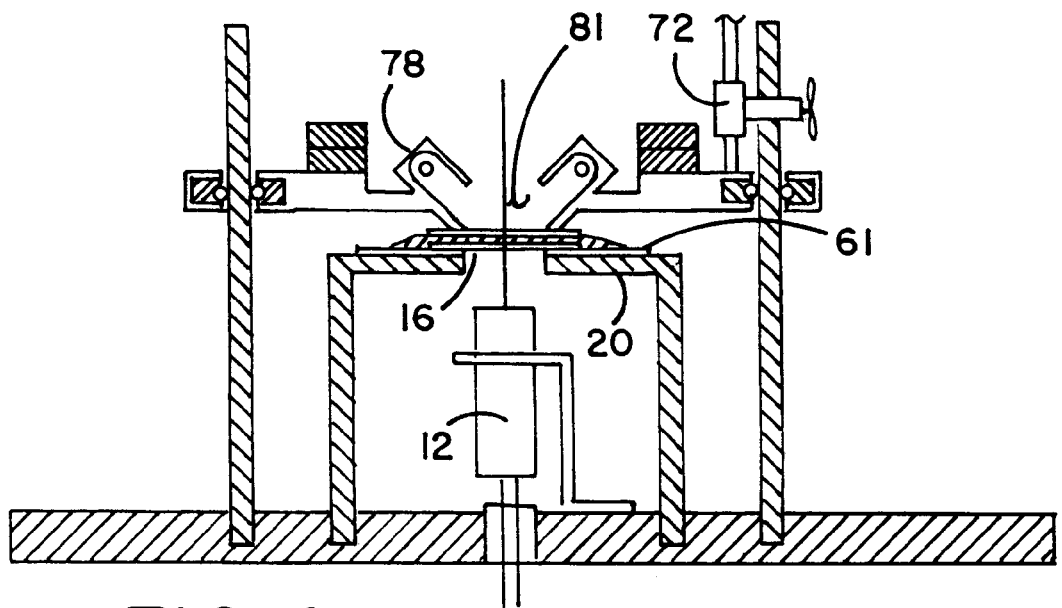
FIG. 4 illustrates the device of FIG. 3 with the sample material melted.
Figure 8:
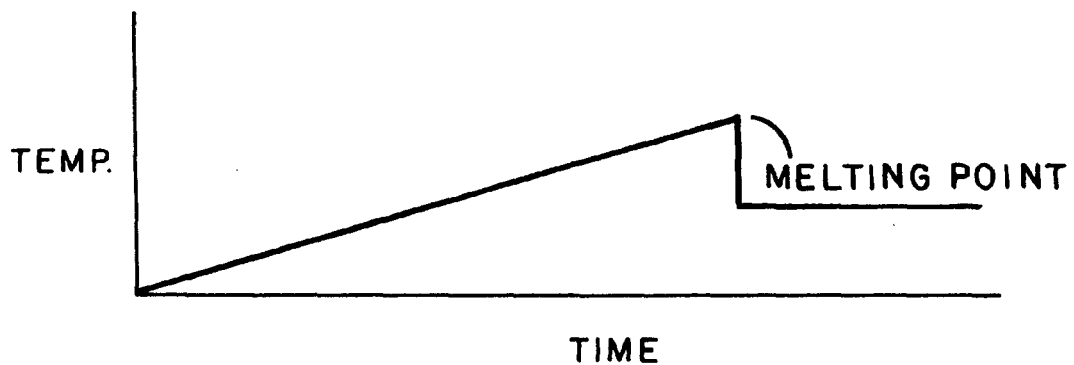
FIG. 8 illustrates a chart showing a typical melting point curve produced by the devices of FIGS. 4 and 6.

FIG. 3 illustrates a further alternate embodiment of the device of this invention. Pressure arm 62 is supported, respectively, by load-bearing member 68. Motion sensor 72 is secured to vertical guide rod 34 by a collar and wing nut assembly so as to be slideably adjustable to position it before a determination is run. Toroidal heating element 78, also disposed on weight support assembly 10, heats sample material 20. At the point in time where the sample material has melted and has been forced by pressure exerted on the upper plate onto collecting disc 61 which is used to catch molten sample material, as seen in FIG. 4, non-contact infrared thermometer 12, because of its narrow field of view, detects no heat coming directly from toroidal heating element 78 as it only senses the empty central area where there is no radiant surface, and there is a drop in the temperature sensed which drop indicates the melting point temperature of the sample material, as seen in the chart of FIG. 8. Toroidal heating element 78, because of its circular configuration leaving an open space immediately above infrared thermometer 12, is not directly sensed by infrared thermometer 12 which instead senses empty space 81 in the center of the toroidal heating element 78 and does not sense the surrounding radiant heating element directly which is out of its field of view.

Figure 5:
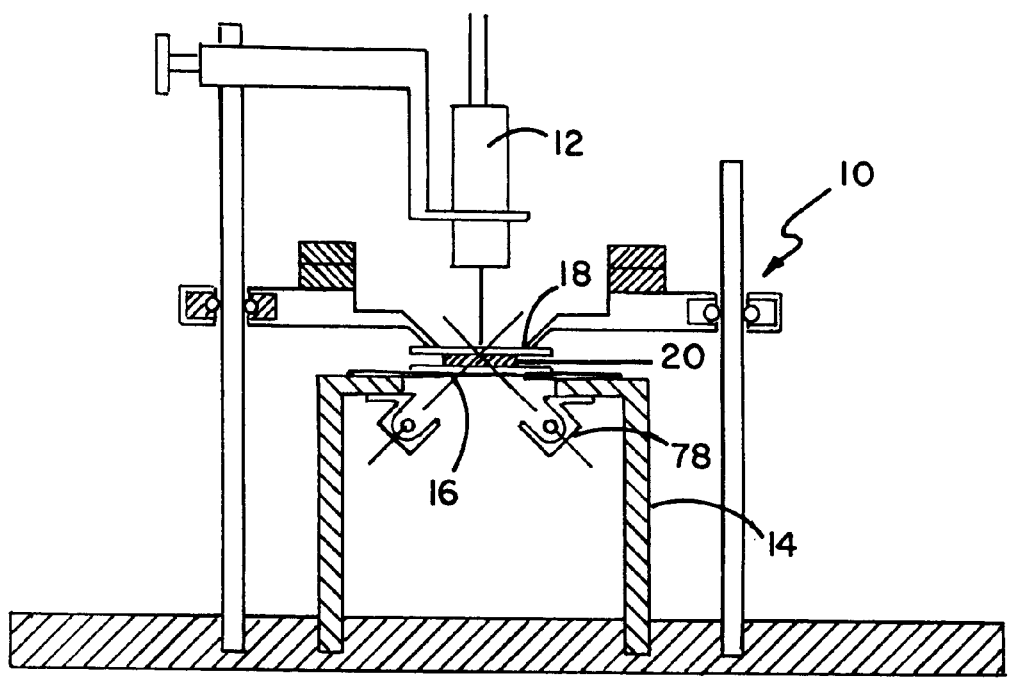
FIG. 5 illustrates a cross-sectional side view of yet another alternate embodiment of the device of this invention.
Figure 6:
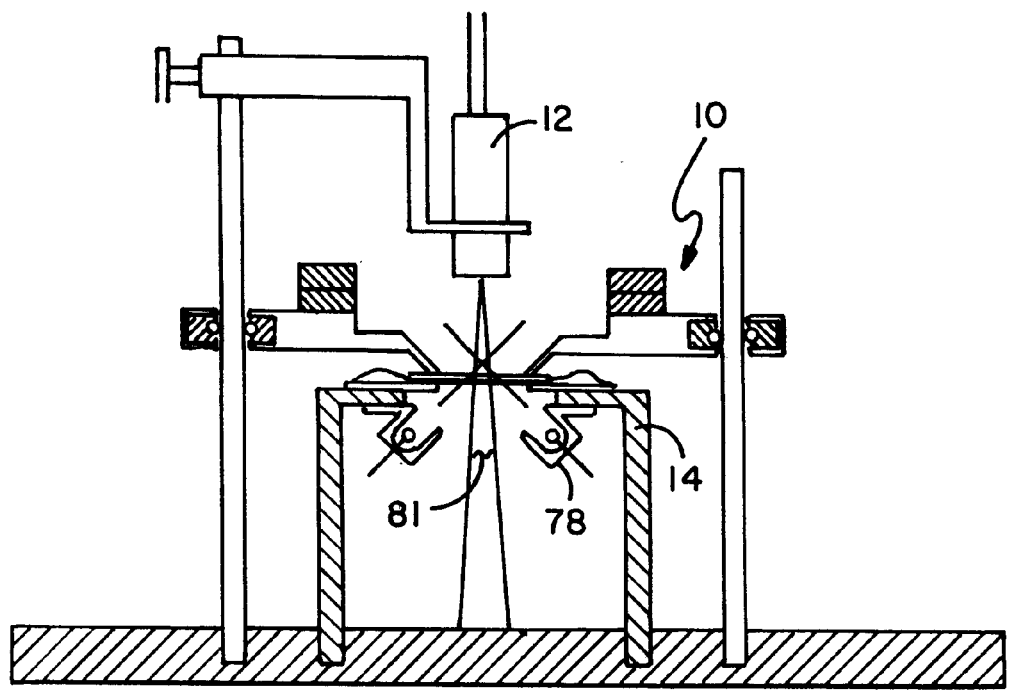
FIG. 6 illustrates the device of FIG. 5 with the sample material melted.
Figure 7:
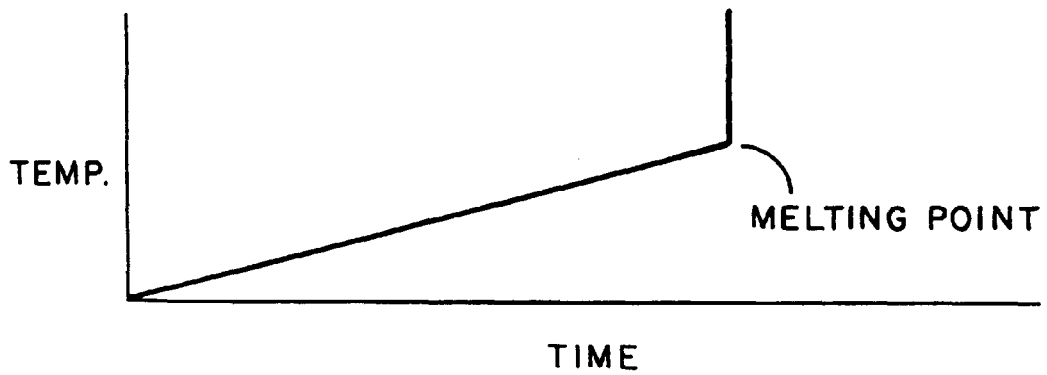
FIG. 7 illustrates a chart showing a typical curve of the recording of a melting point produced by the device of FIG. 2 of this invention.

FIG. 5 illustrates yet another alternate embodiment of that of FIG. 3 with toroidal heating element 78 supported within support member 14 below sample material 20 still held between lower plate 16 and upper plate 18. A similar weight support assembly 10, as in the previous embodiments, applies pressure to the top of upper plate 18. An infrared thermometer 12 senses the sample material as it heats up and when the sample material reaches its melting point, as seen in FIG. 6, the material melts and is forced out the ends of upper and lower plates 18 and 16 by pressure from weight support assembly 10 which leaves the transparent upper and lower plates being sensed by infrared thermometer 12 which does not detect any heat from the toroidal heating element 78 as it only detects through the center empty space 81 of heating element 78 where there is no radiant heating element in the direct line of sight of infrared thermometer 12.

Although the present invention has been described with reference to particular embodiments, it will be apparent to those skilled in the art that variations and modifications can be substituted therefor without departing from the principles and spirit of the invention.

I claim:

1. A device for determining the melting point of a sample material, comprising:

first and second infrared-transparent and transmissive plates, each having first and second ends, sides and a central portion defined between said first and second ends, said first plate disposed adjacent to said second plate with said sample material sandwiched therebetween forming a wafer having a first and second side;

means to support said first and second plates and sample material;

means to apply pressure to said sample material;

heating means to heat said sample material to its melting point, said heating means disposed on said first side of said wafer;

a non-contact infrared thermometer aligned with said heating means for measuring the indicated temperature of said sample material while it is being heated, said infrared thermometer disposed on said second side of said wafer;

said sample material melting when its melting point is reached, said melting causing said sample material to flow out from between said first and second plates and causing said infrared thermometer to sense the higher indicated temperature of said aligned heating means through said first and second plates; and means to record said indicated temperatures over time sensed by said infrared thermometer.

2. A device for determining the melting point of a sample material, comprising:

first and second infrared-transparent and transmissive plates, each having first and second ends, sides and a central portion defined between said first and second ends, said first plate disposed adjacent to said second plate with said sample material sandwiched therebetween forming a wafer having first and second sides;

means to support said first and second plates and sample material;

means to apply pressure to said sample material;

toroidal heating means having a non-heat-producing central portion, said heating means directed to heat said sample material to its melting point, said toroidal heating means disposed on said first side of said wafer;

a non-contact infrared thermometer sensor aligned with said non-heat-producing central portion of said toroidal heating means for measuring the indicated temperature of said sample material while it is being heated, said infrared thermometer disposed on said second side of said wafer;

said sample material melting when its melting point is reached, said melting causing said sample material to flow out from between said first and second plates and causing said infrared thermometer to then sense the lower indicated temperature through said non-heat-producing central portion of said heating means; and means to record said indicated temperature sensed over time by said infrared thermometer.

3. The device of claim 1 wherein said infrared thermometer is positioned below said first and second plates, and said pressure means and said heating means are disposed above said first and second plates.

4. The device of claim 2 wherein said infrared thermometer is positioned below said first and second plates, and said pressure means and said heating means are disposed above said first and second plates.

5. The device of claim 1 wherein said infrared thermometer and said pressure means are positioned above said first and second plates, and said heating means is disposed below said first and second plates.

6. The device of claim 2 wherein said infrared thermometer and said pressure means are positioned above said first and second plates, and said heating means is disposed below said first and second plates.

7. The device of claim 2 wherein said means to apply pressure include a pressure arm that rests on said first plate.

8. The device of claim 5 wherein said means to apply pressure include a pressure arm that rests on said first plate.

9. The device of claim 1 further including means to measure and record movement of said first plate upon the melting of said sample material.

10. The device of claim 2 further including means to measure and record movement of said first plate upon the melting of said sample material.

11. The device of claim 7 further including first and second posts on which said pressure arm is mounted.

12. The device of claim 8 further including first and second posts on which said pressure arm is mounted.

13. The device of claim 11 wherein said pressure means include weights on said pressure arm disposed on said first plate, said weights to be varied according to the desired pressure to be applied to said sample material.

14. The device of claim 12 wherein said pressure means include weights on said pressure arm disposed on said first plate, said weights to be varied according to the desired pressure to be applied to said sample material.

15. The device of claim 1 further including a collecting disc positioned below said second plate for catching melted sample material after its melting point has been reached.

16. The device of claim 2 further including a collecting disc positioned below said second plate for catching melted sample material after its melting point has been reached.

17. A method for determining the melting point of a sample material, comprising the steps of:

providing a sample material;

positioning said sample material between first and second plates having infrared-transparent and transmissive properties;

providing support means for said first and second plates;

providing pressure to said sample material;

providing a heat source;

heating said first and second plates and sample material therebetween by said heat source;

providing an infrared thermometer aligned with said heat source;

sensing the indicated temperature of said sample material by said infrared thermometer;

continuously recording the indicated temperature of said sample material;

melting said sample material to cause it to flow out from between said first and second plates;

sensing said heat source by said infrared thermometer; and detecting a sharp increase in the indicated temperature at the point in time when said sample material melts and flows out from between said first and second plates.

18. A method for determining the melting point of a sample material, comprising the steps of:

providing a sample material;

positioning said sample material between first and second plates having infrared-transparent and transmissive properties;

providing support means for said first and second plates;

providing pressure to said sample material;

providing a heat source;

heating said first and second plates and sample material therebetween by said heat source;

providing an infrared thermometer not aligned with said heat source;

sensing the indicated temperature of said sample material by said infrared thermometer;

continuously recording the indicated temperature of said sample material;

melting said sample material to cause it to flow out from between said first and second plates;

sensing no heat source by said infrared thermometer; and detecting a decrease in the indicated temperature at the point in time when said sample material melts and flows out from between said first and second plates.

* * * * *